United States Patent
Hoenig et al.

(10) Patent No.: US 7,292,893 B2
(45) Date of Patent: Nov. 6, 2007

(54) APPARATUS AND METHOD FOR THE TREATMENT OF INFECTIOUS DISEASE IN KERATINIZED TISSUE

(75) Inventors: Peter A. Hoenig, Sudbury, MA (US); B. Stuart Trembly, Hanover, NH (US)

(73) Assignee: WaveRx, Inc., Waltham, MA (US)

( * ) Notice: Subject to any disclaimer, the term of this patent is extended or adjusted under 35 U.S.C. 154(b) by 0 days.

(21) Appl. No.: 10/845,761

(22) Filed: May 14, 2004

(65) Prior Publication Data
US 2004/0249426 A1    Dec. 9, 2004

Related U.S. Application Data

(60) Provisional application No. 60/471,230, filed on May 16, 2003.

(51) Int. Cl.
*A61F 2/00*    (2006.01)
(52) U.S. Cl. ......................... 607/101; 607/96
(58) Field of Classification Search ........... 606/33; 607/154, 156, 101–102
See application file for complete search history.

(56) References Cited

U.S. PATENT DOCUMENTS

| | | | |
|---|---|---|---|
| 1,636,568 A | 7/1927 | Kennedy | |
| 4,016,886 A | 4/1977 | Doss et al. | |
| 4,092,800 A | 6/1978 | Wayland, Jr. et al. | |
| 4,312,364 A | 1/1982 | Convert et al. | |
| 4,448,198 A | 5/1984 | Turner | |
| 4,679,561 A | 7/1987 | Doss | |
| 4,702,262 A * | 10/1987 | Andersen et al. | 607/155 |
| 4,786,277 A | 11/1988 | Powers et al. | |
| 4,825,880 A | 5/1989 | Stauffer et al. | |
| 4,846,181 A | 7/1989 | Miller | |
| 4,881,453 A | 11/1989 | Armstrong | 92/84 |
| 4,932,420 A * | 6/1990 | Goldstein | 607/156 |
| 4,967,765 A | 11/1990 | Turner et al. | |
| 5,224,927 A | 7/1993 | Tapper | |
| 5,248,478 A | 9/1993 | Kutner et al. | |
| 5,370,676 A * | 12/1994 | Sozanski et al. | 607/101 |
| 5,549,639 A | 8/1996 | Ross | |
| 5,708,445 A | 1/1998 | Moller et al. | |
| 5,741,317 A | 4/1998 | Ostrow | |
| 5,947,956 A | 9/1999 | Karell | |
| 6,006,136 A | 12/1999 | Glucksman | |
| 6,051,018 A * | 4/2000 | Larsen | 607/96 |
| 6,056,744 A * | 5/2000 | Edwards | 606/41 |

(Continued)

FOREIGN PATENT DOCUMENTS

WO    WO 2003095018 A3    3/2004

(Continued)

OTHER PUBLICATIONS

Tanaka, Y. et al. *Yonaga Acta Medica*, 41: 83-88, 1998.

(Continued)

*Primary Examiner*—Roy D. Gibson
(74) *Attorney, Agent, or Firm*—Lowrie, Lando & Anastasi, LLP

(57) ABSTRACT

The invention provides methods for the treatment of keratinized tissue infected with a pathogen. The invention utilizes electromagnetic energy, particularly microwave energy, as a treatment means to reduce the amount of or eliminate the pathogen from the keratinized tissue.

50 Claims, 2 Drawing Sheets

U.S. PATENT DOCUMENTS

| | | | |
|---|---|---|---|
| 6,078,842 A | | 6/2000 | Gross et al. |
| 6,090,788 A | * | 7/2000 | Lurie ........................... 514/23 |
| 6,104,959 A | * | 8/2000 | Spertell ...................... 607/101 |
| 6,254,389 B1 | * | 7/2001 | Seghatol ..................... 433/215 |
| 6,283,956 B1 | | 9/2001 | McDaniel |
| 6,330,471 B1 | | 12/2001 | Higo et al. |
| 6,413,255 B1 | | 7/2002 | Stern |
| 6,463,336 B1 | | 10/2002 | Mawhinney |
| 6,629,971 B2 | | 10/2003 | McDaniel |
| 6,635,055 B1 | | 10/2003 | Cronin |
| 6,663,659 B2 | | 12/2003 | McDaniel |
| 6,676,655 B2 | | 1/2004 | McDaniel |
| 6,696,677 B2 | | 2/2004 | Kennedy |
| 6,723,090 B2 | * | 4/2004 | Altshuler et al. ............... 606/9 |
| 6,878,147 B2 | * | 4/2005 | Prakash et al. ............... 606/33 |
| 6,960,201 B2 | | 11/2005 | Cumbie |
| 7,137,979 B2 | | 11/2006 | Conrad et al. |
| 2002/0169442 A1 | * | 11/2002 | Neev .............................. 606/9 |
| 2003/0023284 A1 | | 1/2003 | Gartstein et al. |
| 2003/0153962 A1 | | 8/2003 | Cumbie |
| 2003/0180181 A1 | * | 9/2003 | Greib et al. ................... 422/22 |
| 2004/0093042 A1 | * | 5/2004 | Altshuler et al. ............. 607/88 |
| 2004/0138708 A1 | | 7/2004 | Tucek |
| 2004/0151716 A1 | | 8/2004 | Hamer et al. |
| 2004/0243181 A1 | | 12/2004 | Conrad et al. |
| 2005/0080465 A1 | * | 4/2005 | Zelickson et al. ............. 607/88 |
| 2005/0149124 A1 | | 7/2005 | Brogan et al. |
| 2006/0004425 A1 | | 1/2006 | Cumbie |
| 2006/0106427 A1 | | 5/2006 | Brogan et al. |
| 2006/0173515 A1 | | 8/2006 | Cumbie |
| 2006/0212098 A1 | | 9/2006 | Demetriou et al. |
| 2006/0241729 A1 | | 10/2006 | Dawson |

FOREIGN PATENT DOCUMENTS

| | | |
|---|---|---|
| WO | WO 2004/107956 A2 | 12/2004 |
| WO | WO 2004107956 A3 | 3/2006 |

OTHER PUBLICATIONS

Korpan, N. et al. *J. Surg. Res.*, 57(6): 667-71, Dec. 1994.

Deacon, J.W. *Introduction to Modern Mycology*. 2nd Ed. Blackwell Scientific Pubs, 1984.

Bold, H.C. et al. *Morphology of Plants and Fungi*, 5th Ed. (1987).

Moritz and Henriques. *Am. J. Pathology*. 23: 695-720 (1947).

Song, C.W. "Role of Blood Flow in Hyperthermia." in M. Urano and E.B. Douple (Eds.), *Hyperthermia and Oncology vol. 3: Interstitial Hyperthermia—Physics Biology and Clinical Aspects*. Utrecht, the Netherlands, VSP BV, 1992.

Dahl (Dahl, O.) "Interaction of Heat and Drugs In Vitro and In Vivo," *Thermoradiotherapy and Thermochemotherapy, vol. 1: Biology, Physiology and Physics*. Berlin: Springer-Verlag, 1995.

Ryan, T.P., "Comparison of Six Microwave Antenna for Hyperthermia Treatment of Cancer: SAR Results for Single Antennas and Arrays," *Int. J. Radiation Oncology, Biology and Physics*, 21: 403-413, 1991.

Baker et al. (1969) *PhytopathologyPhytopathology* 59(2)193-197.

Swicord et al. (1981) *IEEE Trans. On Microwave Theory and Techniques* 29(11):1202-1208.

Ludeke et al. (1983) *Journal of Microwave Power* 18(3):277-283.

Trembly et al. (1991) *IEEE Transactions On Biomedical Engineering* 28(1)85-91.

Lagunas-Solar et al. (1994) Annual International Research Conference on Methyl Bromide Alternatives and Emissions Reductions, Nov. 13-16, Kissimmee, Florida.

Ramo et al. *Fields and Waves In Communication Electronics*, 3rd Ed. (New York, 1994).

Jones et al. (1995) *Pacific Rim Biotechnology Conference* Melbourne, Australia, Feb. 1995.

Ferreira et al. (1996) *Fungal Genetics Newsletter* 43:25-26.

Guyton et al. (1996) *Textbook of Medical Physiology* p. 919.

Lantis et al. (1998) *Surg. Endosc.* 12:170-176.

Tanaka et al. (1998) *Yonaga Acta Medica* 41:83-88.

Hay (2001) *British Journal of Dermatology* 145(S60):3-11.

Mandell et al. *Principles and Practice of Infectious Diseases*, Fifth Edition, Chapter 257 by Hay, R.J., p. 2765.

Kalinowski et al. Presented Apr. 18, 2003. The use of low voltage direct current as a . . .

Edsberg et al. Presented Feb. 12, 2003. In Vitro and In Vivo Outcomes with the Use . . .

* cited by examiner

APPARATUS AND METHOD FOR THE TREATMENT OF INFECTIOUS DISEASE IN KERATINIZED TISSUE

RELATED APPLICATION

This application claims the benefit of U.S. Provisional Application No. 60/471,230, filed May 16, 2003, which is incorporated by reference in its entirety.

BACKGROUND OF THE INVENTION

1. Field of the Invention

The present invention relates to the field of medicine, particularly the treatment of infectious diseases. More specifically, the invention relates to treatment of keratinized tissue infected with fungi and/or bacteria.

2. Summary of the Related Art

Infectious diseases of keratinized tissues are a difficult problem for medical treatment. Keratins are a class of scleroprotein that serve as the major protein components of hair, wool, nails, the organic matrix of the enamel of teeth, horns, hoofs, and the quills of feathers. These proteins generally contain large quantities of the sulfur-containing amino acids, particularly cysteine. Keratins provide a tough, fibrous matrix for the tissues in which they are found. These proteins are characterized as being extremely water insoluble. Because keratins contain few polar amino acids, there is little or no moisture content in the tissues they form. This presents difficulties for the medical treatment of infected keratinized tissues because medicaments are not easily delivered into this type of tissue.

By way of example, onychomycosis is clinically defined as an infection of the nail plate caused by any fungus, including dermatophytes, nondermatophytes and yeasts. This disease accounts for up to 50% of all nail disease and affects 2% to 18% or more of the world's population. There are four clinical types of onychomycosis: (1) distal subungual onychomycosis, (2) proximal subungual onychomycosis, (3) white superficial onychomycosis, and (4) candidal onychomycosis. The target sites for the treatment of onychomycosis reside in the nail plate, nail bed and nail matrix. Characteristically, infected nails coexist with normal-appearing nails.

Microwave irradiation is an efficient means of sterilization. For example, U.S. Pat. No. 4,092,800 teaches the sterilization of soil with microwave irradiation. Baker K. F. et al. (*Phytopathology* 59(2):193–197 (1969)) teach the sterilization of garbage with microwave irradiation. Lagunas-Solar M. C. et al. teach the sterilization of food with microwave irradiation (Food and Agriculture Applications of Pulsed Power Technologies as Alternatives to Methyl Bromide, presented at the 1994 Annual International Research Conference on Methyl Bromide Alternatives and Emissions Reductions. Nov. 13–16 (1994) Kissimme, Fla., and Tanaka Y. et al. (*Yonaga Acta medica* 41:83–88 (1998)) teach the sterilization of towels with microwave irradiation.

Lantis J. C. et al. (*Surg. Endosc.* 12:170–176 (1998)) teach that microwave energy has been used in medicine for many clinical applications since the development of reliable magnetrons in the 1960's. Microwave energy therapy has been used for the treatment of malignant and benign neoplasia. It is being explored as a modality to improve the healing of infected wounds. It is being studied as a therapy for the treatment of duodenal ulcer disease, benign prostatic hypertrophy and for heart disease. Microwave energy is also being used to warm diasylate fluid for continuous ambulatory peritoneal dialysis and as a way to sterilize docking connectors. Ferreira, A. V. B. and Glass, N. L. (*Fungal Genetics Newsletter* No. 43:25–26 (1996)) and Jones, C. L. et al. (4$^{th}$ Pacific Rim Biotechnology Conference, Melbourne, Australia, Feb. (1995)) teach that microwave energy has proven to be useful in DNA extraction protocols from different eukaryotes. In addition, U.S. Pat. No. 4,881,543 teaches that microwave energy therapy can be used to correct myopia in the human eye.

The most common form of treatment for onychomycosis is the oral administration of Terbinafine (Novartis International AG, Basel, Switzerland) or Itraconazole (Janssen Pharmaceutica Products, L.P., Titusville, N.J.). These drugs dominate the current market for the treatment of onychomycosis, estimated by Datamonitor at $1.4 billion in the year 2000.

However, there is a need for the development of other forms of treatment. Hay R. J. (*British Journal of Dermatology* 145(S60):3–11(2001)) teaches that these drugs have a clinical failure rate of approximately 25–40%. In addition, both drugs carry label precautions about potential organ toxicity and interactions with common prescription and non-prescription drugs. The Physicians Desk Reference (2003) teaches that rare cases of hepatic failure (including death) have been reported following oral treatment with Terbinafine and Itraconazole. Rare cases of serious cardiovascular events, including death, also have been associated with Itraconazole (Id.). Treatment times are long (several months) and costly. Hay, R. J. (supra) teaches that 5–10% of the nail surface still remains abnormal even with a full cure (defined by negative re-culturing). Mandell et al. (*Principles and Practice of Infectious Diseases*, Fifth edition, Chapter 257 by Hay R. J., page 2765) teach that remission rates are above 60%. Treatment options using topical agents are usually of little benefit, and chemical or surgical removal of the infected nail(s) are not adequate therapies, since these treatments can lead to nail bed shrinkage and dorsal dislocation of the nail bed.

Thus, there remains a need in the art to develop improved methods for the treatment of infected tissues containing high amounts of keratin.

BRIEF SUMMARY OF THE INVENTION

The invention provides an apparatus and methods for the medical treatment of keratinized tissue infected with a pathogen. The methods according to the invention enable an efficient, non-invasive medical treatment with little or no side effects. The inventors have surprisingly discovered that the high water content of fungi and bacteria relative to keratinized tissue makes them sensitive to electromagnetic energy, particularly microwave energy. This results in "superheating" and explosion of the bacterial and/or fungal cells. There may also be additional, therapeutically beneficial, non-thermal effects of electromagnetic energy, e.g., microwave energy, on bacteria and/or fungi.

In a first aspect, the invention provides a method for treating keratinized tissue infected with a pathogen. The method comprises exposing the tissue to electromagnetic energy thereby killing the pathogen infecting the keratinized tissue. In some embodiments, the pathogen is a fungus. In some embodiments the pathogen is a bacterium.

In certain embodiments, the electromagnetic energy is microwave energy. In some embodiments, the electromagnetic energy is infrared energy or millimeter waves. In certain embodiments, the microwave energy has a wave frequency from about 10 MHz to about 30 GHz.

In some embodiments, the infected keratinized tissue is nail tissue, the corneum stratum of epidermis, hair tissue, hoof tissue, horny tissue, or teeth. In certain embodiments, the infected keratinized tissue is from a mammal, such as for example, human, bovine, or equine tissue. In particularly preferred embodiment, the keratinized tissue is human keratinized tissue infected with a pathogen. In one specific embodiment, the nail tissue is human nail tissue.

In some embodiments, the method includes placing an adaptor over or in contact with the tissue to be treated. The function of the adaptor is to smooth over the heating distribution in the treated tissue. Such an adaptor may be comprised of plastic, for example but not limited to, teflon, nylon, delrin, which may be obtained from Small Parts, Inc., Miami Lakes, Fla.; McMaster Carr Company, Dayton, N.J.; or MSC Company, Melville, N.Y.

In a second aspect, the invention provides an applicator for the delivery of electromagnetic energy to keratinized tissue infected with a pathogen. The applicator comprises more than one metallic conductor separated by a distance much less than half a wavelength and a flexible substrate to allow conformance to a curved surface.

In certain embodiments, the applicator further comprises an adhesive to permit adherence to a surface. Such adhesives are well known in the art. In some embodiments, the metallic conductors and substrate are sufficiently thin to permit trimming to an arbitrary shape in a plane with an instrument such as shears.

In certain embodiments, the applicator has from about 2 to about 40 metallic conductors. In some embodiments, the metallic conductors of the applicator have a length from about 5 to about 40 mm and a width of about 0.25 mm to about 2 mm. In some embodiments, the applicator has an interdigitated geometry. In certain of these embodiments, the metallic conductors are spaced about 0.25 mm to about 2 mm. In some embodiments, the applicator has 2 conductors having a spacing of about 0.25 mm to 2 mm which meander in the plane defined by the surface of the tissue to be heated. In some embodiments, the applicator has a single conductor having the shape of a horn of diameter about 2 mm to 40 mm.

In some embodiments of the second aspect, one or more conductors have spiral geometry. In some embodiments, pairs of conductors have dipole geometry. In some embodiments, each conductor of the applicator has waveguide geometry. In some embodiments, one or more conductors have meandering geometry. In certain embodiments, a pair or pairs of conductors have transmission line geometry.

In some embodiments, the applicator further comprises a cable, e.g., a coaxial cable. In some embodiments, the applicator further comprises a cable, e.g., coaxial cable, and an electromagnetic energy source. In certain embodiments, the electromagnetic energy source is selected from the group consisting of a magnetron and solid state oscillator. In some embodiments, the applicator comprises a waveguide instead of a cable.

DETAILED DESCRIPTION OF THE PREFERRED EMBODIMENTS

Figure 1:
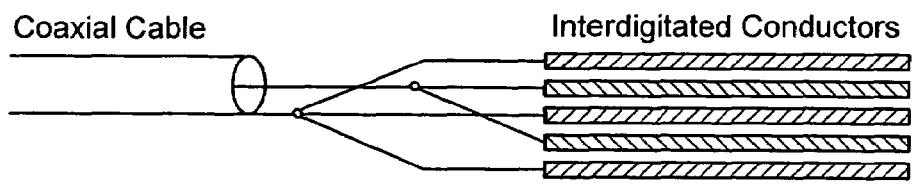
FIG. 1 is a schematic representation of one example of an applicator of the invention.

The invention relates to methods for the treatment of keratinized tissue infected with a pathogen. The present inventors have surprisingly discovered that electromagnetic energy, particularly microwave energy, is a therapeutic treatment for keratinized tissue infected with a pathogen. The invention also provides an applicator for the delivery of electromagnetic energy to keratinized tissue infected with a pathogen. The issued patents, patent applications, and references that are cited herein are hereby incorporated by reference to the same extent as if each was specifically and individually indicated to be incorporated by reference. In the event of inconsistencies between any teaching of any reference cited herein and the present specification, the latter shall prevail for purposes of the invention.

Advantages of the use of electromagnetic energy, e.g., microwave energy, are the speed, efficiency, localized effect, ability to intervene without surgery, and absence of toxic, hazardous or polluting residues. Fungi and bacteria are unlikely to develop resistance to this type of treatment as they can to antifungal or antibacterial medication. There have been no reports of fungi or bacteria developing resistance to, for example, microwave energy.

In a first aspect, the invention provides a method for treating keratinized tissue infected with a pathogen. The method comprises contacting the tissue with electromagnetic energy thereby killing the pathogen infecting the keratinized tissue. In some embodiments, the pathogen is a fungus. In some embodiments the pathogen is a bacterium.

As used herein, the term "keratinized tissue" means a tissue having a scleroprotein as the principal constituent, such as epidermis, hair, nails, horny tissues and the organic matrix of the enamel of the teeth.

In certain embodiments, the electromagnetic energy is microwave energy. In some embodiments the electromagnetic energy is infrared energy or millimeter waves. The microwave frequency band is only loosely defined in engineering practice. Here, it is defined to mean the range from about 10 MHz to about 10 GHz. However, other frequencies outside this range are not excluded. Thus, in certain embodiments the microwave energy has a wave frequency from about 10 MHz to about 30 GHz. As used herein, millimeter waves are defined as having a frequency of 30 to 3,000 GHz. As used herein, infrared energy is defined as energy having a wavelength of 0.1 to 0.00072 millimeters.

The term "about" as used herein refers to a variance of 20% for the lower and higher values. For example, if a numerical range is given as from about 10 to about 20, it will be understood that the lower value may range from 8 to 12 and the higher value may range from 16 to 24.

By way of non-limiting example, microwave energy can be coupled into keratinized tissue by bringing metallic conductors into proximity or contact with it. The depth of penetration of microwave energy into tissue can be controlled by the spacing of the metallic conductors in contact with the tissue. In this way, the depth of penetration can be set to a value suited to the anatomical site of treatment.

The greatest depth of penetration would be attained by a plane wave of microwave energy, where the actual value would be determined by the frequency of radiation and the water content of tissue. For example, Ramo S. et al. (*Fields and Waves in Communication Electronics*, 3$^{rd}$ Ed. (New York (1994)) teach that the depth of penetration of a plane wave of 915 MHz radiation in soft tissue other than fat would be approximately 20 millimeters. Thus, a plane wave of microwave energy may be useful for the treatment of keratinized tissue that is thick, e.g. a hoof.

If it is undesirable to heat tissue at such a depth, the metallic conductors can be arranged so that a plane wave is not produced. Swicord, M. L. and Davis, C. C. (*IEEE Trans. On Microwave Theory And Techniques* 29(11):1202–1208 (1981)) teach that closely-spaced metallic conductors in proximity to tissue produce a fringing pattern of microwave fields that penetrate a lesser distance, the total distance being determined by the spacing of metallic conductors. As used herein, "closely-spaced" means much less than a half-wavelength. This method has been applied successfully, for example, to heat the cornea of the eye without over-heating the endothelial cells on the posterior surface of the cornea. Trembly B. S. and Keates R. H. (*IEEE Transactions on Biomedical Engineering* 38(1):85–91 (1991)) teach that in this case the penetration of microwave 915 MHz energy was restricted to a few tenths of a millimeter to suit the anatomy.

The same technique would be appropriate for heating a thin layer of keratinized tissue, such as a nail, across its narrow dimension from a position in contact or proximity to its surface.

The methods described herein do not rely on a conduction current flowing through tissue from a metallic conductor in contact with tissue (resistive heating). Instead, the methods described herein use either a plane wave of electromagnetic energy, e.g. microwave energy, or a fringing electric field of electromagnetic energy, e.g., microwave energy, from the closely-spaced metallic conductors to penetrate a controlled distance into tissue. The rapidly-oscillating field causes polar molecules, such as water in fungal or bacterial cells, to rotate in place, thereby producing local frictional heating. This mechanism permits transmission of energy through tissue of low water content, which is effectively an electrical insulator.

It is important to control the depth of penetration of the electric fields in the case of heating a nail, for example, because the derma of the nail bed must not receive a significant thermal dose. The derma of the nail bed has a high water content, and will absorb electromagnetic energy, e.g., microwave energy, if a significant field has penetrated to that depth. Closely-spaced metallic conductors (described herein) protect the underlying dermal tissue by limiting the depth of penetration.

In some embodiments, the infected keratinized tissue is nail tissue, the corneum stratum of epidermis, hair tissue, hoof tissue, horny tissue, or teeth. In certain embodiments, the infected keratinized tissue is from a mammal, such as for example, human, bovine, or equine tissue. In particularly preferred embodiment, the keratinized tissue is human keratinized tissue infected with a pathogen. In one specific embodiment, the keratinized tissue is human nail tissue.

The characteristic high blood perfusion of skin tissue affords further protection from thermal damage because the continuous transport of blood at body temperature into the local capillary bed is an effective cooling mechanism. Furthermore, Guyton, A. C. and Hall, J. E. (*Textbook of Medical Physiology* pg. 919 (Philadelphia: 1996)) teach that perfusion of skin is a function of temperature, increasing as temperature increases.

In some embodiments, the methods of the invention can include the step of inducing reactive hyperemia, wherein blood perfusion after a period of enforced low perfusion increases to a level higher than before the intervention (Id. at pg. 202). In practice, pressure could be applied to the toe to restrict blood perfusion before the heat treatment. After the release of pressure, the resulting increased perfusion would provide enhanced cooling during the period of microwave heating.

It would be desirable to measure the temperature of tissue during the course of a treatment. In addition to surface measurement, it may be advantageous to exploit the phenomenon of microwave radiometry. Lüdeke K. M. and Köhler J. (*Journal of Microwave Power* 18(3):277–283 (1983)) teach that the natural electromagnetic emissions of an object can be correlated with its temperature. This method can be used to sense the temperature below the surface of the body, for example, in the derma of the nail bed. The tissue temperature signal could form part of a feedback loop that could assure the safety and efficacy of the heat treatment described above.

In a second aspect, the invention provides an applicator for the delivery of electromagnetic energy to keratinized tissue infected with a pathogen. The applicator comprises more than one metallic conductor separated by a distance much less than half a wavelength and a flexible substrate to allow conformance to a curved surface.

As used herein, the term "much less than half" refers to less than or equal to 0.25 times a wavelength.

In certain embodiments, the applicator further comprises an adhesive to permit adherence to a surface. Such adhesives are well known in the art. In some embodiments, the metallic conductors and substrate are sufficiently thin to permit trimming to an arbitrary shape in a plane with an instrument such as shears.

As used herein, the term "metallic conductor" refers to material or an object that permits an electric current to flow easily. In specific embodiments, the metallic conductors will be made of copper, brass, silver, gold, aluminum, or stainless steel.

In certain embodiments, the applicator has from about 2 to about 40 metallic conductors. In some embodiments, the metallic conductors of the applicator have a length from about 5 to about 40 mm and a width of about 0.25 mm to about 2 mm. In some embodiments, the applicator has an interdigitated geometry having a spacing between metallic conductors of about 0.25 mm to about 2 mm. In some embodiments, the applicator has 2 conductors having a spacing of about 0.25 mm to 2 mm which meander in the plane defined by the surface of the tissue to be heated. In some embodiments, the applicator has a single conductor having the shape of a horn of diameter about 2 mm to 40 mm. Metallic conductors can be obtained from, e.g., Small Parts, Inc., Miami Lakes, Fla.

In some embodiments of the second aspect, one or more conductors have spiral geometry. In some embodiments, pairs of conductors have dipole geometry. In some embodiments, each conductor of the applicator has waveguide geometry. In some embodiments, one or more conductors have meandering geometry. In certain embodiments, a pair or pairs of conductors have transmission line geometry.

In some embodiments, the applicator further comprises a coaxial cable. In some embodiments, the applicator further comprises a coaxial cable and an electromagnetic energy source. In certain embodiments, the electromagnetic energy source is selected from the group consisting of a magnetron and solid state oscillator. Cables can be obtained from, e.g., Belden Wire and Cable, Richmond, Ind. Energy sources can be obtained from, e.g., Radio Research Instrument Co., Waterbury, Conn.

Figure 3:
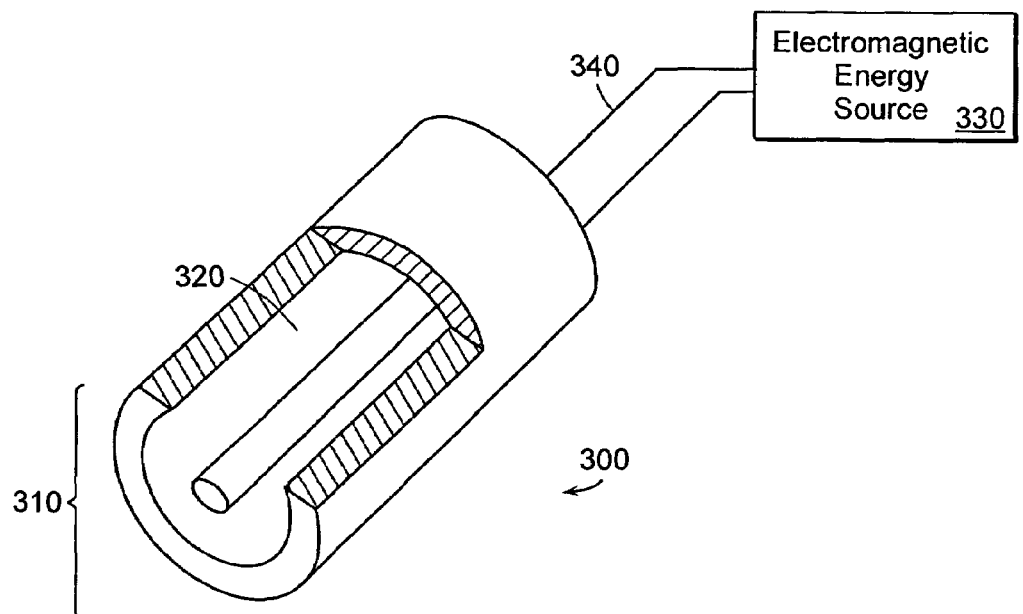
FIG. 3 is a schematic of an applicator 300 comprising a coaxial cable 310 with only a portion 320 of an outer conductor removed and an electromagnetic energy source 330 in electrical communication with the coaxial cable 310 through a cable 340.
Figure 4:
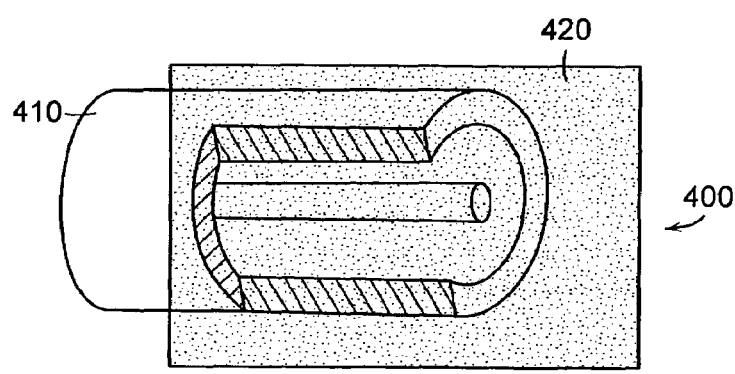
FIG. 4 is a schematic of an applicator 400 comprising a coaxial cable 410 with an adaptor 420 coupled to the coaxial cable 410.

In certain embodiments, an applicator adapted for external delivery of electromagnetic energy to a keratinized tissue infected with a pathogen is disclosed. Referring to FIG. 3, in some embodiments the applicator 300 comprises a coaxial cable 310 with only a portion of an outer conductor removed and comprises a single aperture for delivery of the electromagnetic energy to the keratinized tissue. Referring to FIG. 4, in some embodiments the applicator may comprise an adaptor 420 coupled to a coaxial cable 410, that is configured to provide the electromagnetic energy from the coaxial cable to the keratinized tissue. In some embodiments, the applicator may comprise a coaxial cable with only a portion of an outer conductor removed and an adaptor that is constructed and arranged to smooth the distribution of the electromagnetic energy provided to the keratinized tissue.

In some embodiments, the applicator includes an adaptor to be placed over or in contact with the tissue to be treated. The function of the adaptor is to smooth over the heating distribution in the treated tissue. Such an adaptor may be comprised of plastic, for example but not limited to, teflon, nylon, delrin, which may be obtained from, e.g., Small Parts, Inc., Miami Lakes, Fla., McMaster Carr Company, Dayton, N.J.; or MSC Company, Melville, N.Y.

By way of non-limiting example, a practical example of closely-spaced metallic conductors would be an interdigitated geometry designed to cover the surface of a nail (FIG. 1). With this specific embodiment, the metallic conductors are connected through a cable or other means to a source of electromagnetic energy, such as a magnetron or solid state oscillator.

Figure 2:
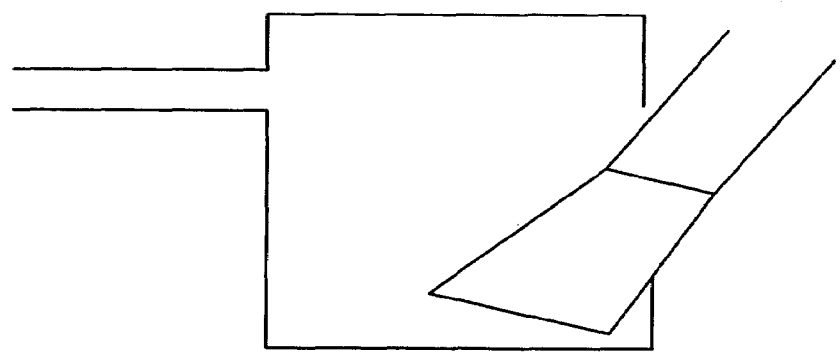
FIG. 2 is a schematic representation of one example of an applicator of the invention.

In an alternative embodiment, the metallic conductors may form a partially or completely closed chamber that surrounds the tissue, e.g., a hoof, which is the configuration of a microwave oven. For example, with the applicator shown in FIG. 2, electromagnetic energy enters a central cavity through a cable or waveguide from the left. Next, a hoof is inserted from right into the applicator, and electromagnetic energy is supplied for treatment.

The examples below are intended to further illustrate certain preferred embodiments of the invention, and are not intended to limit the scope of the invention.

EXAMPLES

Example 1

Preliminary Testing

Two examples were performed: 1) *Trichophyton rubrum* was isolated from nail tissue and was identified at Emerson Hospital Mycology Lab by conventional methods. The fungus was plated on BBL Sab Dex Emmons dish (CM41, Oxoid Inc., Ogdensburg, N.Y.) and exposed to 2450 MHz at 1100 watts (Panasonic Household Microwave Oven NN-S668BA) for varying lengths of time. No growth was found at exposures greater than 10 seconds. 2) Toe nail clippings that had previously been shown by periodic acid schiff stain (PAS) to contain fungus were exposed to 2450 MHz at 1100 watts of microwave energy for varying lengths of time. Fungal isolation was carried out at room temperature on BBL Sab Dex Emmons dish (CM41, Oxoid Inc., Ogdensburg, N.Y.) with and without chloramphenicol (0.05 g/L) and cycloheximide (5 g/L). After 21 days of culturing, no growth was seen at exposures greater than 1 minute.

Example 2

Applicator Testing

The electromagnetic energy applicator, e.g. a microwave energy applicator, is evaluated for heating fungal cells in keratinized tissue by heating a target of tissue-equivalent material. This material consists of two layers, an upper one that simulates the nail and a lower one that simulates the soft tissue of the toe. In order to simulate tissue for purposes of electromagnetic energy, e.g., microwave energy, heating, it is necessary to employ a material or mixture of materials with the same dielectric constant and electrical conductivity as tissue; mixtures (tissue phantoms) to simulate soft tissue are described in the literature (Hartesgrove, G., et al., *Bioelectromagnetics* 8:29–36 (1987). If materials to simulate the nail cannot be found in the literature, an eviscerated nail will be used. The tissue equivalent materials are assembled so as to approximate the anatomy of, for example, human tissue.

The temperature at the interface between the simulated nail and underlying skin are measured. For example, a microwave-immune, fiber optic temperature sensor (Luxtron, Corp., Santa Clara, Calif.) is used for this purpose, since a metal sensor, such as a thermocouple, perturbs the microwave field and is subject to self-heating. Alternatively, a layer of liquid crystal could be used at this interface to quantify the temperature elevation. Liquid crystal changes color with temperature, and color is associated with temperature through calibration in a water bath and analysis of the color in stored digital images by commercial software (e.g., Adobe Photoshop). The layer of liquid crystal is visualized through the translucent soft-tissue phantom during the experiment. The liquid crystal could be on a mylar backing or in the form of a paint spread on the under surface of the nail or simulated nail (Edmund Scientific, Inc., Tonawanda, N.Y.). The lower portion of the simulated tissue assembly is immersed in a temperature-controlled water bath to elevate it to body temperature.

The electromagnetic energy applicator, e.g., microwave energy applicator, is constructed with closely-spaced metallic conductors intended to limit the depth of penetration of microwave energy. This will be placed against the nail or simulated nail, and the applicator will be tuned with a conventional double stub tuner to minimize reflected power. The reflection of power is characteristic of microwave systems, especially those including an applicator with closely-spaced metallic conductors. By minimizing reflected power, more energy is transferred into the target tissue.

A constant value of electromagnetic energy, e.g., microwave energy, is applied, and then temperature data is acquired over time at the interface between the simulated soft tissue and nail. This will be done with a data acquisition system or a video camera, as determined by the type of temperature sensor. The experiment is repeated for several values of electromagnetic energy, e.g., microwave energy, in order to create a chart of temperature elevation above body temperature at the skin-nail interface for various values of time and energy applied. This series of experiments is then repeated with two other electromagnetic energy identical to the first except for different values of spacing between metallic conductors.

The object of these experiments is to quantify the performance of a family of electromagnetic energy, e.g., microwave energy applicators, in support of the experiments in vivo to follow. Specifically, the experiments permits the selection of an applicator and set electromagnetic energy, e.g., microwave energy, so as to deliver a safe thermal dose to the skin beneath the nail, where thermal dose is defined by an empirical function of temperature and exposure time. This empirical function and the maximum thermal dose for skin tissue can be found in the literature (Song, C. W., *Cancer Research* 44 (10):4721–4730 (1984); Fajardo L. F., *Cancer Research* 44 (10):4826–4835 (1984)).

The temperature that is measured in these experiments is higher than in living tissue, due to the action of blood perfusion. Blood perfusion is an effective cooling mechanism, especially in skin tissue. There is no known method for simulating the effect of cooling by blood perfusion, due to the difficulty of replicating the five micron diameter of capillaries, where most heat transfer takes place. Consequently, the heating protocol in the following in vivo experiments is conservative, in the sense that the living skin temperature during treatment is lower than what we measured in these experiments. If it is found that fungal cells cannot be destroyed in vivo by the protocol established herewith, the in vivo tissue is re-treated with incrementally greater microwave energy with the knowledge than blood perfusion tends to protect skin tissue beneath the nail from significant temperature elevation. This is particularly true, since skin perfusion itself may increase as local temperature increases. Nonetheless, electromagnetic energy, e.g., microwave energy, is increased in small increments on the order of approximately 10% and further increases are not made until the safety of the protocol is established through examinations of the subjects during the follow-up period.

Example 3

Determination of a Kill-Dose Microwave Energy Level

The prototype microwave applicator is used on fungal infected eviscerated human nail to establish a kill-dose of electromagnetic energy, e.g., microwave energy. A kill-dose is defined as the microwave energy needed to kill the fungi such that it can no longer grow or replicate. The parameters of the electromagnetic energy, e.g., microwave energy, applicator is equal to or less than the safe thermal dose as defined by the experiments conducted in Example 2. The kill-dose is a maximum dose. Future experiments in vivo may show that only limited exposure to electromagnetic energy, e.g., microwave energy, is enough to cure the onychomycosis.

The following methods were used: The dermatophyte was obtained from the clipped toe nail sample of a human patient with clinically diagnosed onychomycosis. Fungus was confirmed in the sample by microscopy with the PAS stain, and cultured onto Sabouraud's dextrose agar with/without chloramphenicol and cycloheximide for 4 weeks, identifying the fungus as a *Trichophyton* spp.

Using sterile technique the nail samples were prepared using a # 11 scalpel to scrape off the white keratin debris from the infected nail. 4 mm lengths of nail debris was then loaded into sterilized 2 mm diameter polyurethane tubing and closed with phenolic plugs. A total of 51 samples were made.

The vial to be treated was placed within a plexiglass vial carrier designed to position the nail sample at one of the locations of the maximum electric field inside of a slotted line (Hewlett Packard Model 805C). This apparatus consists of an 11 mm diameter cylindrical inner conductor fixed centrally between two vertical plates that together form the outer conductor. The electric field is greatest at the point of closest approach between the inner and outer conductors, a gap of 4.5 mm. The slotted line was terminated with an open circuit, producing a standing wave pattern along the long axis of the slotted line. The axial location of a maximum of electric field was measured with the electric field probe integral to the slotted line. A maximum was found at a distance equal to a half-wavelength (164 mm) from the point of the open circuit termination, as predicted by transmission line theory.

The slotted line was driven by a 915 MHz generator (American Microwave Technologies Model 1120) through 6 feet of RG-214/U cables. The generator in turn was controlled by a purpose-built proportional-integral controller that compared the set-point of power to the actual value measured by a dual directional coupler (Narda Model 3020A) and power meter (Hewlett Packard Model 435B). The generator was protected from reflected power by a circulator (Pamtech Model 1146) terminated with a load (Narda Model 369 BNF, 175 watt rating). Samples contained in vials 1 to 25 were exposed to 5 minutes of heating with a forward power of 68 watts. Samples in vials 26 to 51 were controls.

The samples were then separately inoculated onto Dermatophyte Test Medium (Acu-DTM, Acuderm, Inc., Ft. Lauderdale, Fl.). They were incubated at room temperature. The test medium was examined for color change and colony growth daily for two weeks. A positive result was declared when the test medium changed from yellow to red with or without concurrent colony growth. A negative result was declared when there was no color change.

Of the treated samples, after 14 days, $1/25$ showed the presence of viable dermatophytes. Of the control samples, after 14 days, $13/25$ showed the presence of viable dermatophytes. There was no colony growth noted without color change on the DTM medium. There was no color change without colony growth.

A chi-squared analysis of the data was performed. Using an alpha level of 0.05 there was a significant difference in the growth proportions across the 2 treatment conditions. In addition, the effect size (Cramer's V) is high.

At 30 days the samples were reexamined. There was no new growth among the treated samples, and 2 additional samples among the controls showed growth.

This experiment suggests that there is strong evidence that 68 Watts, for 5 minutes, of microwave irradiation in the slotted line apparatus described above, is a kill-dose for a dermatophyte, *Trichophyton* spp., in a keratin substrate.

The main part of the experiment was stopped after 14 days because color interpretation of the Dermatophyte Test Medium is questionable after this due to the possibility of false positives and fewer than 2% of cultures require 2 weeks to show a change in color. The 30 day evaluation was used to answer the question of whether the irradiation delayed growth rather than provide a kill-dose.

The low growth rate is consistent with the previously described 30% positive microscopy and culture results due to sampling errors from infected nails. This was higher in our experiment probably because of the particularly small sample size required by the 2 mm diameter polyurethane tubing.

EQUIVALENTS

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A method for treating keratinized tissue infected with a fungus comprising exposing the tissue to an effective amount of microwave energy to kill the fungus infecting the keratinized tissue.

2. The method of claim 1, wherein the microwave energy has a wave frequency from about 10 MHz to about 30 GHz.

3. The method of claim 1, wherein the infected keratinized tissue is nail tissue.

4. The method of claim 3, wherein the nail tissue is human nail tissue.

5. The method of claim 1, wherein the keratinized tissue is the stratum corneum of epidermis tissue.

6. The method of claim 1, wherein the keratinized tissue is hair.

7. The method of claim 1, wherein the keratinized tissue is horny tissue.

8. The method of claim 1, wherein the method further includes a step to promote cooling of underlying tissue by way of reactive hyperemia.

9. The method of claim 1, wherein the method further includes a step to measure tissue temperature by way of microwave radiometry.

10. The method of claim 1, wherein the exposing step comprises exposing the keratinized tissue with an effective amount of microwave energy to heat the fungus.

11. The method of claim 1, wherein the exposing step comprises providing the microwave energy at a power to superheat the fungus.

12. The method of claim 1, wherein the exposing step comprises exposing the keratinized tissue to a plane wave of microwave energy.

13. The method of claim 1, wherein the exposing step comprises providing the microwave energy for at least about 1 minute.

14. The method of claim 1, wherein the exposing step comprises providing the electromagnetic energy at a frequency of about 10 MHz to about 10 GHz.

15. A method for treating keratinized tissue infected with a fungus comprising exposing the tissue to an effective amount of millimeter wave energy to kill the fungus infecting the keratinized tissue.

16. The method of claim 15, wherein the infected keratinized tissue is nail tissue.

17. The method of claim 16, wherein the nail tissue is human nail tissue.

18. The method of claim 15, wherein the keratinized tissue is the stratum corneum of epidermis tissue.

19. The method of claim 15, wherein the keratinized tissue is hair.

20. The method of claim 15, wherein the keratinized tissue is horny tissue.

21. The method of claim 15, wherein the method further includes a step to promote cooling of underlying tissue by way of reactive hyperemia.

22. The method of claim 15, wherein the method further includes a step to measure tissue temperature by way of microwave radiometry.

23. The method of claim 15, wherein the exposing step comprises exposing the keratinized tissue with an effective amount of millimeter energy to heat the fungus.

24. The method of claim 15, wherein the exposing step comprises providing the millimeter wave energy at a power to superheat the fungus.

25. The method of claim 15, wherein the exposing step comprises exposing the keratinized tissue to a plane wave of millimeter wave energy.

26. The method of claim 15, wherein the exposing step comprises providing the millimeter wave energy for at least about 1 minute.

27. An applicator adapted for external delivery of electromagnetic energy to a keratinized tissue infected with a pathogen comprising:
   a coaxial cable with only a portion of an outer conductor removed and, comprising a single aperture for delivery of the electromagnetic energy to the keratinized tissue; and
   an adaptor coupled to the coaxial cable that is configured to provide the electromagnetic energy from the coaxial cable to the keratinized tissue.

28. The applicator of claim 27, further comprising a waveguide.

29. The applicator of claim 27, further comprising an electromagnetic energy source coupled to the applicator.

30. The applicator of claim 29, wherein the electromagnetic energy source is selected from the group consisting of a magnetron and a solid state oscillator.

31. The applicator of claim 29, further comprising a cable coupled to the applicator and the electromagnetic energy source.

32. The applicator of claim 27, in which the adaptor is constructed and arranged to be placed externally in contact with the keratinized tissue.

33. The applicator of claim 27, in which the coaxial cable is rigid and configured for non-invasive treatment of the keratinized tissue.

34. The applicator of claim 27, in which the adaptor is flexible to allow conformance to a curved or irregular surface.

35. The applicator of claim 27, in which the adaptor is constructed and arranged to direct the electromagnetic energy to the keratinized tissue.

36. The applicator of claim 27, in which the adaptor is constructed and arranged to reduce electromagnetic energy to tissue surrounding the keratinized tissue.

37. The applicator of claim 27, in which the adaptor comprises an adhesive to permit adherence to a surface.

38. The applicator of claim 27, in which a part of the adaptor is constructed and arranged to permit trimming to an arbitrary shape.

39. An applicator adapted for external delivery of electromagnetic energy to a keratinized tissue infected with a pathogen comprising:
   a coaxial cable with only a portion of an outer conductor removed; and
   an adaptor coupled to the coaxial cable that is configured to provide the electromagnetic energy from the coaxial cable to the keratinized tissue, in which the adaptor is constructed and arranged to smooth the distribution of the electromagnetic energy provided to the keratinized tissue.

40. The applicator of claim 39, further comprising a waveguide.

41. The applicator of claim 39, further comprising an electromagnetic energy source coupled to the applicator.

42. The applicator of claim 41, wherein the electromagnetic energy source is selected from the group consisting of a magnetron and a solid state oscillator.

43. The applicator of claim 41, further comprising a cable coupled to the applicator and the electromagnetic energy source.

44. The applicator of claim 39, in which the adaptor is constructed and arranged to be placed externally in contact with the keratinized tissue.

45. The applicator of claim 39, in which the coaxial cable is rigid and configured for non-invasive treatment of the keratinized tissue.

46. The applicator of claim 39, in which the adaptor is flexible to allow conformance to a curved or irregular surface.

47. The applicator of claim 39, in which the adaptor is constructed and arranged to direct the electromagnetic energy to the keratinized tissue.

48. The applicator of claim 39, in which the adaptor is constructed and arranged to reduce electromagnetic energy to tissue surrounding the keratinized tissue.

49. The applicator of claim 39, in which the adaptor comprises an adhesive to permit adherence to a surface.

50. The applicator of claim 39, in which a part of the adaptor is constructed and arranged to permit trimming to an arbitrary shape.

* * * * *